(12) United States Patent
Utagawa et al.

(10) Patent No.: US 8,820,933 B2
(45) Date of Patent: Sep. 2, 2014

(54) IMAGING APPARATUS AND IMAGING METHOD

(75) Inventors: Tsutomu Utagawa, Yokohama (JP); Makoto Sato, Tokyo (JP); Yukio Sakagawa, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/634,527

(22) PCT Filed: Mar. 29, 2011

(86) PCT No.: PCT/JP2011/001868
§ 371 (c)(1),
(2), (4) Date: Sep. 12, 2012

(87) PCT Pub. No.: WO2011/122004
PCT Pub. Date: Oct. 6, 2011

(65) Prior Publication Data
US 2013/0003018 A1    Jan. 3, 2013

(30) Foreign Application Priority Data
Mar. 31, 2010 (JP) .................................. 2010-082804

(51) Int. Cl.
 A61B 3/14 (2006.01)
 A61B 3/10 (2006.01)
 A61B 3/00 (2006.01)
(52) U.S. Cl.
 USPC ............................ 351/206; 351/205; 351/246

(58) Field of Classification Search
 USPC .................................................. 351/200–246
 See application file for complete search history.

(56) References Cited

U.S. PATENT DOCUMENTS

| | | |
|---|---|---|
| 5,321,501 A | 6/1994 | Swanson et al. |
| 6,198,540 B1 | 3/2001 | Ueda et al. |
| 2008/0084538 A1 | 4/2008 | Maeda et al. |
| 2008/0100612 A1 | 5/2008 | Dastmalchi et al. |
| 2008/0151187 A1 | 6/2008 | Tsukada et al. |
| 2010/0226554 A1* | 9/2010 | Suehira .......................... 382/131 |
| 2012/0320338 A1* | 12/2012 | Hirose et al. .................. 351/206 |

FOREIGN PATENT DOCUMENTS

| | | |
|---|---|---|
| CN | 101115436 A | 1/2008 |
| CN | 101563017 A | 10/2009 |
| EP | 1908397 A2 | 4/2008 |
| EP | 1935329 A1 | 6/2008 |
| JP | 2008508068 A | 3/2008 |
| JP | 2008086670 A | 4/2008 |
| JP | 2009-160190 A | 7/2009 |
| JP | 2010-035607 A | 2/2010 |

* cited by examiner

Primary Examiner — Mohammed Hasan
(74) Attorney, Agent, or Firm — Canon USA Inc. IP Division

(57) ABSTRACT

An imaging apparatus according to the present invention can cause a display unit to display a scanning range of each of a plurality of measurement light beams in an intersection image (an image in a direction intersecting a direction in which an inspection object is irradiated with the plurality of measurement light beams) of the inspection object.

29 Claims, 11 Drawing Sheets

| 202 | IMAGING MODE | NUMBER OF "A" SCANS | NUMBER OF "B" SCANS | "x" RANGE | "y" RANGE | NUMBER OF BEAMS | NUMBER OF TIMES OF IMAGING | IMAGING TIME |
|---|---|---|---|---|---|---|---|---|
| ○ | MODE 1 | 500 | 500 | 10 | 10 | 3 | 1 | 2.08 |
| ● | MODE 2 | 300 | 300 | 10 | 10 | 3 | 1 | 0.75 |
| ○ | MODE 3 | 100 | 100 | 10 | 10 | 1 | 5 | 1.00 |
| ○ | MODE 4 | 500 | 500 | 6 | 6 | 3 | 1 | 2.08 |
| ○ | MODE 5 | 300 | 300 | 6 | 6 | 3 | 1 | 0.75 |
| ○ | MODE 6 | 300 | 100 | 6 | 6 | 1 | 5 | 1.25 |
| ○ | MODE 7 | 2000 | 1 | 10 | - | 3 | 25 | 1.00 |
| ○ | MODE 8 | 500 | 1 | 6 | - | 3 | 50 | 0.50 |

| 202 | IMAGING MODE | NUMBER OF "A" SCANS | NUMBER OF "B" SCANS | "x" RANGE | "y" RANGE | NUMBER OF BEAMS | NUMBER OF TIMES OF IMAGING | IMAGING TIME |
|---|---|---|---|---|---|---|---|---|
| ○ | MODE 1 | 500 | 500 | 10 | 10 | 3 | 1 | 2.08 |
| ● | MODE 2 | 300 | 300 | 10 | 10 | 3 | 1 | 0.75 |
| ○ | MODE 3 | 100 | 100 | 10 | 10 | 1 | 5 | 1.00 |
| ○ | MODE 4 | 300 | 300 | 6 | 6 | 1 | 1 | 1.80 |
| ○ | MODE 5 | 100 | 100 | 6 | 6 | 1 | 5 | 1.00 |
| ○ | MODE 6 | 100 | 100 | 6 | 6 | 1 | 20 | 4.00 |
| ○ | MODE 7 | 2000 | 1 | 10 | - | 1 | 25 | 1.00 |
| ○ | MODE 8 | 500 | 1 | 6 | - | 1 | 50 | 0.50 |

| 202 | IMAGING MODE | NUMBER OF "A" SCANS | NUMBER OF "B" SCANS | "x" RANGE | "y" RANGE | NUMBER OF BEAMS | NUMBER OF TIMES OF IMAGING | IMAGING TIME |
|---|---|---|---|---|---|---|---|---|
| ○ | MODE 1 | 500 | 500 | 10 | 10 | 3 | 1 | 2.08 |
| ○ | MODE 2 | 300 | 300 | 10 | 10 | 3 | 1 | 0.75 |
| ○ | MODE 3 | 100 | 100 | 10 | 10 | 1 | 5 | 1.00 |
| ● | MODE 4 | 300 | 500 | 6 | 6 | 1 | 1 | 1.80 |
| ○ | MODE 5 | 100 | 300 | 6 | 6 | 1 | 5 | 1.00 |
| ○ | MODE 6 | 100 | 100 | 6 | 6 | 1 | 20 | 4.00 |
| ○ | MODE 7 | 2000 | 1 | 10 | - | 1 | 25 | 1.00 |
| ○ | MODE 8 | 500 | 1 | 6 | - | 1 | 50 | 0.50 |

| 202 | IMAGING MODE | NUMBER OF "A" SCANS | NUMBER OF "B" SCANS | "x" RANGE | "y" RANGE | NUMBER OF BEAMS | NUMBER OF TIMES OF IMAGING | IMAGING TIME |
|---|---|---|---|---|---|---|---|---|
| ● | MODE 1 | 500 | 300 | 9 | 6 | 1 | 1 | 3.00 |
| ○ | MODE 2 | 300 | 300 | 10 | 10 | 3 | 1 | 0.75 |
| ○ | MODE 3 | 100 | 100 | 10 | 10 | 1 | 5 | 1.00 |
| ○ | MODE 4 | 300 | 300 | 6 | 6 | 1 | 1 | 1.80 |
| ○ | MODE 5 | 100 | 100 | 6 | 6 | 1 | 5 | 1.00 |
| ○ | MODE 6 | 100 | 100 | 6 | 6 | 1 | 20 | 4.00 |
| ○ | MODE 7 | 2000 | 1 | 10 | - | 1 | 25 | 1.00 |
| ○ | MODE 8 | 500 | 1 | 6 | - | 1 | 50 | 0.50 |

IMAGING APPARATUS AND IMAGING METHOD

TECHNICAL FIELD

The present invention relates to an imaging apparatus and an imaging method, and more particularly, to an imaging apparatus and an imaging method that captures an image of an object to be inspected using a plurality of measurement light beams.

BACKGROUND ART

In recent years, an imaging apparatus (hereinafter, sometimes referred to as an optical coherence tomography (OCT) apparatus) that captures a tomographic image (hereinafter, sometimes referred to as an optical coherence tomographic image) of an inspection object using an optical coherence tomography (OCT) utilizing interference by a low-coherence light has been used in the medical field, particularly in the ophthalmic field. Since an OCT apparatus utilizes the properties of light, the OCT apparatus can acquire tomographic images at high resolution on a micrometer base which is an order of wavelength of light.

When a fundus of a subject's eye is measured, for example, an examinee may sometimes move, blink, or make slight movement (involuntary eye movement during visual-fixation) at random during measurement. For this reason, there is an issue that the tomographic image of the subject's eye acquired by the OCT apparatus will be distorted.

In order to acquire a three-dimensional structure of a pupil at a high speed, an OCT which irradiates the pupil (anterior eye portion) with a plurality of measurement light beams is discussed in Japanese Unexamined Patent Application Publication (Translation of PCT Application) No. 2008-508068. Since an irradiating region per one measurement light beam can be narrowed, the three-dimensional structure can be captured at a high speed.

CITATION LIST

Patent Literature

[PTL 1] Japanese Unexamined Patent Application Publication (Translation of PCT Application) No. 2008-508068

SUMMARY OF INVENTION

Technical Problem

Relating to an imaging apparatus that captures optical coherence tomographic images of an object to be inspected using a plurality of measurement light beams, it is desired to improve controllability for each measurement light beam (or for each optical coherence tomographic image) from a viewpoint of user's convenience. In the art described above, there are no discussions relating to improvement of the user's convenience, and relating to improvement of the controllability for each measurement light beam.

Solution to Problem

According to an aspect of the present invention, an imaging apparatus includes an irradiation unit configured to irradiate an inspection object with a plurality of measurement light beams, an intersection image acquisition unit configured to acquire an intersection image of the inspection object in a direction intersecting a direction in which the inspection object is irradiated with the plurality of measurement light beams, an intersection image display control unit configured to cause a display unit to display the intersection image, and a scanning range display control unit configured to cause the display unit to display a scanning range of the plurality of measurement light beams by being associated with the intersection image.

According to another aspect of the present invention, an imaging apparatus capable of capturing optical coherence tomographic images of an inspection object based on a plurality of combined light beams each obtained by combining a plurality of return light beams from the inspection object irradiated with a plurality of measurement light beams and a plurality of reference light beams each corresponding to the plurality of measurement light beams includes a selection unit configured to select at least one of a plurality of imaging modes with different imaging conditions, and an acquisition unit configured to acquire the optical coherence tomographic images according to the imaging mode selected by the selection unit.

According to yet another aspect of the present invention, a method for capturing optical coherence tomographic images of an inspection object based on a plurality of combined light beams each obtained by combining a plurality of return light beams from the inspection object irradiated with a plurality of measurement light beams and a plurality of reference light beams each corresponding to the plurality of measurement light beams includes displaying an intersection image of the inspection object in a direction intersecting a direction in which the inspection object is irradiated with the plurality of measurement light beams, and displaying a scanning range of the plurality of measurement light beams on the display unit by being associated with the intersection image.

According to yet another aspect of the present invention, a method for capturing optical coherence tomographic images of an inspection object based on a plurality of combined light beams each obtained by combining a plurality of return light beams from the inspection object irradiated with a plurality of measurement light beams and a plurality of reference light beams each corresponding to the plurality of measurement light beams includes selecting at least one from among a plurality of imaging modes with different imaging conditions, and acquiring the optical coherence tomographic images according to the selected imaging mode.

An imaging apparatus according to the present invention can cause a display unit to display scanning ranges of a plurality of measurement light beams by being associated with intersection images of an inspection object. Accordingly, controllability can be improved for each measurement light beam (or for each optical coherence tomographic image), and the imaging apparatus with good convenience for the user can be provided.

Further features and aspects of the present invention will become apparent from the following detailed description of exemplary embodiments with reference to the attached drawings.

BRIEF DESCRIPTION OF DRAWINGS

The accompanying drawings, which are incorporated in and constitute a part of the specification, illustrate exemplary embodiments, features, and aspects of the invention and, together with the description, serve to explain the principles of the invention.

DESCRIPTION OF EMBODIMENTS

Figure 1A:
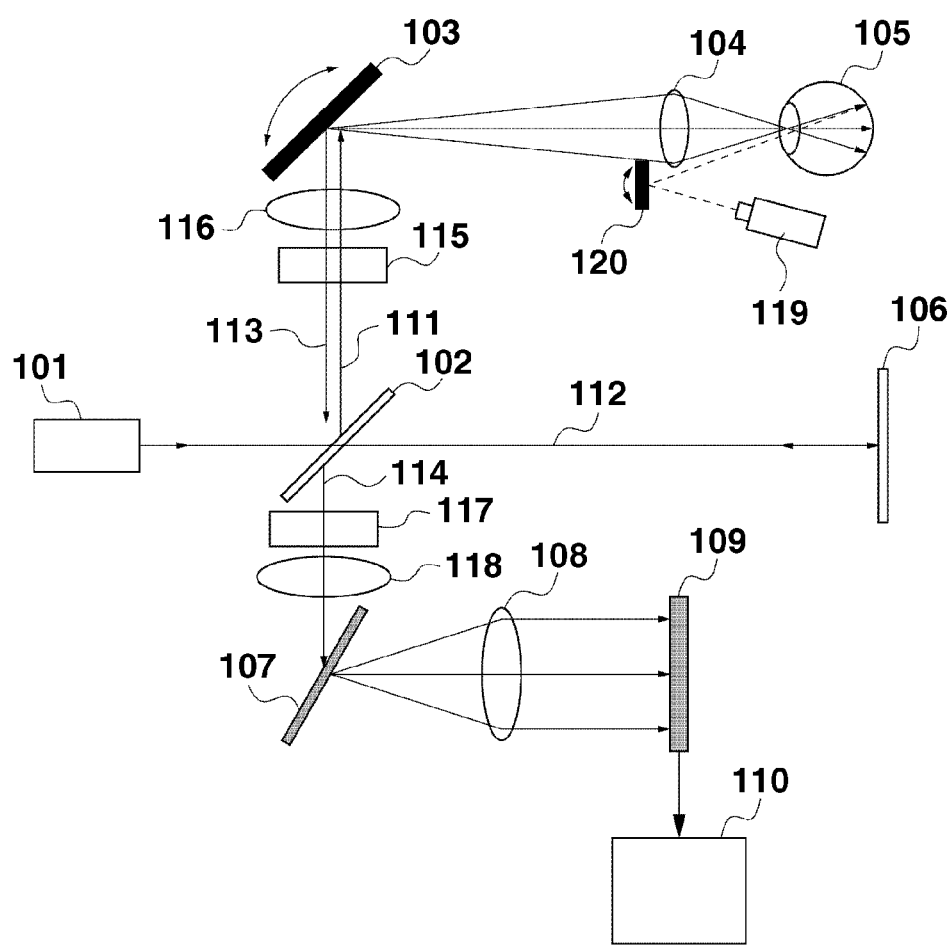
FIG. 1A illustrates an imaging apparatus according to a first exemplary embodiment of the present invention.

Various exemplary embodiments, features, and aspects of the invention will be described in detail below with reference to the drawings.

An imaging apparatus according to the exemplary embodiment of the present invention can cause a display unit to display an intersection image (an image in a direction intersecting to a direction to which a plurality of measurement light beams is irradiated to an inspection object) of an inspection object in such a manner that each scanning range of the plurality of measurement light beams is indicated therein. Accordingly, controllability can be improved for each measurement light beam (or for each optical coherence tomographic image), and thus the imaging apparatus with good convenience for the user can be provided.

Here, the intersection image refers to at least one of a two-dimensional image on a surface of an eye fundus (sometimes referred to as a fundus image), an integrated image in which at least a portion of the optical coherence tomographic image is integrated in a depth direction of the fundus, and an optical coherence tomographic image (sometimes referred to as a C scan image) in a substantially vertical direction to the depth direction of the fundus. The imaging apparatus according to the present invention includes an intersection image acquisition unit that acquires the above-described intersection images, and an intersection image display control unit that causes the display unit to display the above-described intersection images.

Further, the imaging apparatus according to the present invention includes a scanning range display control unit that causes the display unit to display scanning ranges of the plurality of measurement light beams by being associated with the above-described intersection images. It is desirable to cause the display unit to display the scanning ranges of the plurality of measurement light beams with different colors or shapes respectively. Accordingly, each of the scanning ranges can be indicated so as to allow a user to recognize the respective correspondences of the scanning ranges and the plurality of measurement light beams. The above-described scanning range can be interpreted as a scanning position, a scanning region, an irradiating position, an imaging region, or the like.

Further, the imaging apparatus according to the present invention preferably includes a tomographic image display control unit that causes the display unit to display each of the optical coherence tomographic images. Further, the imaging apparatus according to the present invention preferably includes a position display control unit that causes the display unit to display a position of each of the optical coherence tomographic images by being associated with the above-described intersection image.

Further, the imaging apparatus according to the present invention preferably includes a selection unit that selects at least one of a plurality of imaging modes with different imaging conditions. Thus, the optical coherence tomographic images can be acquired according to the imaging mode selected by the above-described selection unit.

Figure 2A:
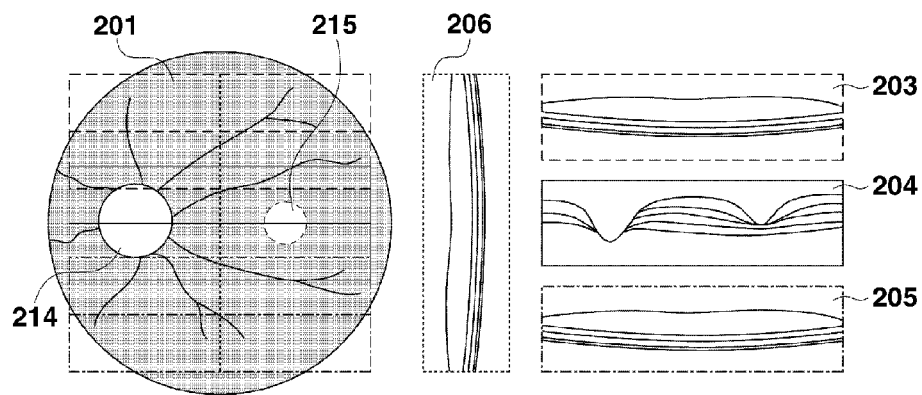
FIG. 2A illustrates a screen display according to the first exemplary embodiment.
Figure 2B:
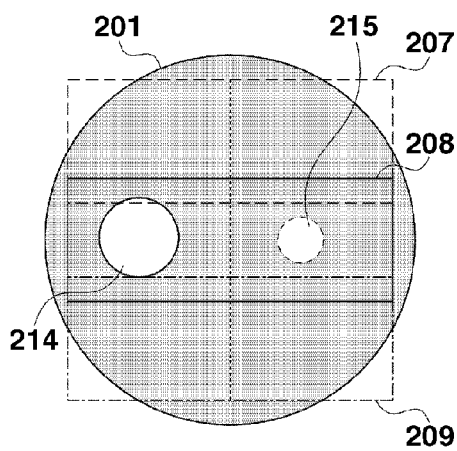
FIG. 2B illustrates a screen display according to the first exemplary embodiment.

Further, it is preferable from a viewpoint of convenience for the user that the imaging apparatus includes an imaging condition display control unit that causes the display unit to display a list of the above-described plurality of imaging modes and images having a function of the above-described selection unit (e.g., an icon or a region 202 displayed on a display portion in FIGS. 2A and 2B. Any configuration may be used as long as a preset function can be operated, when it is clicked or dragged with a cursor displayed on the display portion). The display unit may be integrated with the imaging apparatus, or may be removably mounted to the imaging apparatus. Further, the display unit may communicate with the imaging apparatus via wired or wireless connection.

In the imaging apparatus, at least one imaging mode among the above-described plurality of imaging modes is preferably set such that the number of the measurement light beams with which an inspection object is irradiated is different from that in the other imaging modes. Also, at least one imaging mode among the above-described plurality of imaging modes is preferably set such that at least one value among a size of scanning range, the number of times of imaging, and an imaging time period is different from those in the other imaging modes.

A configuration for implementing the present invention will be described below with reference to the drawings.

The imaging apparatus according to a first exemplary embodiment will be described with reference to FIG. 1A. FIG. 1A is a block diagram illustrating an OCT apparatus according to the present exemplary embodiment. The OCT apparatus that uses three measurement light beams as a plurality of measurement light beams with which an inspection object such as a subject's eye is irradiated will be described. For simplification of the drawings, three measurement light beams are drawn collectively as one light beam. The present exemplary embodiment uses an optical fiber, when the plurality of measurement light beams is transmitted, but the present invention is not limited to the optical fiber. In addition, the present exemplary embodiment is applied to a spectral domain (SD)-OCT, but the present invention can be applied to another type of OCT (such as, time domain (TD)-OCT and swept source (SS)-OCT) and a scanning laser ophthalmoscope (SLO).

First, three light beams emitted from a light source 101 are divided each into reference light beams 112 and measurement light beams 111 by a beam splitter 102. Three measurement light beams 111, after a position of an optical fiber end which transmits three light beams has is adjusted by a position adjusting device 115 at the fiber end, are irradiated to an XY mirror 103 via a lens 116. The XY mirror 103 is reciprocally rotated to perform raster scanning of the fundus as an observation target with the measurement light beams 111 according to a command from a controller (not illustrated) which controls the entire apparatus.

Three measurement light beams 111 reflected by the XY mirror 103 each are irradiated to an eye 105 as the observation target. The measurement light beams 111 irradiated to the eye 105 are reflected or scattered at the fundus and returned as return light beams 113. Then, the return light beams are irradiated to the beam splitter 102 via the lens 116, and combined with the reference light beams 112 by the beam splitter 102 to form three interference light beams 114 (sometimes referred to as a combined light).

The three interference light beams 114 are incident on a diffraction grating 107 via a lens 118, are dispersed by the diffraction grating 107, and each form an image by the lens 108 on a line sensor 109. In the apparatus, a three-line sensor including three photoelectric conversion element arrays is used, but an area sensor may be used. Three pieces of image information corresponding to three interference light beams which are photoelectrically converted by the line sensor 109 each are subjected to analogto-digital (A/D) conversion in an image information processing unit 110, and then are subjected to Fourier transform. Further, tomographic images (sometimes referred to as optical coherence tomographic images) of the fundus of the eye 105 are acquired by combining the three pieces of image information.

Next, a periphery of the light source 101 will be described. The light source 101 is a super luminescent diode (SLD) as a typical low-coherent light source. The light source 101 has a wavelength of 840 nm, and a band width of 50 nm. The band width is an important parameter, since it has an effect on resolution in an optical axis direction of the tomographic images to be obtained.

Although the SLD is selected here as a type of the light source, amplified spontaneous emission (ASE) or the like may be used, as long as it can emit low-coherent light. Considering that an eye is to be measured, near-infrared light is suitable for a wavelength of the light source. Moreover, it is desirable that a wavelength as short as possible, since the wavelength of the light source affects resolution in a horizontal direction of the tomographic images to be obtained. Thus, in this case, a light source having a wavelength of 840 nm is used. Other wavelengths may be selected depending on a measurement area of the observation target.

The reference light beams 112 divided by the beam splitter 102 are reflected by the mirror 106, and return to the beam splitter 102. By making an optical path length of the reference light beam 112 to be the same as a length of the measurement light beam 111, the reference light beam and the measurement light beam can interfere with each other. Three pieces of the mirror 106 are prepared to correspond to three reference light beams 112, and a position of each mirror can be independently adjusted, but in the present exemplary embodiment, for simplification of the drawing, the mirror 106 is illustrated as one mirror.

The measurement light beams 111 divided by the beam splitter 102 are incident on the XY mirror 103. Here, for simplification of the drawing, the XY mirror 103 is drawn as one mirror, but actually two mirrors, namely an X scanning mirror and a Y scanning mirror, are arranged close to each other. The measurement light beams 111 are used for raster scanning on a retina of the eye 105 in a direction perpendicular to the optical axis via a lens 104. The lens 104 is used to collect the measurement light beams 111 onto the retina. A zoom lens which can adjust a focal distance may be used for the lens 104. By the optical system described above, when the measurement light beams 111 enter the eye 105, the measurement light beams 111 are reflected and scattered on the retina of the eye 105 and become the return light beams 113.

Figure 4A:
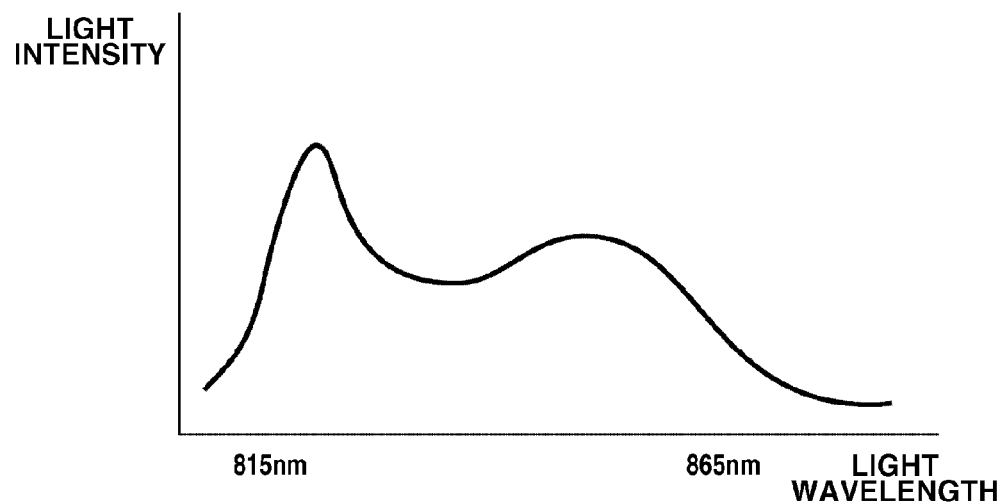
FIG. 4A illustrates frequency characteristics of a light source and an output signal of a sensor according to the first exemplary embodiment.
Figure 4B:
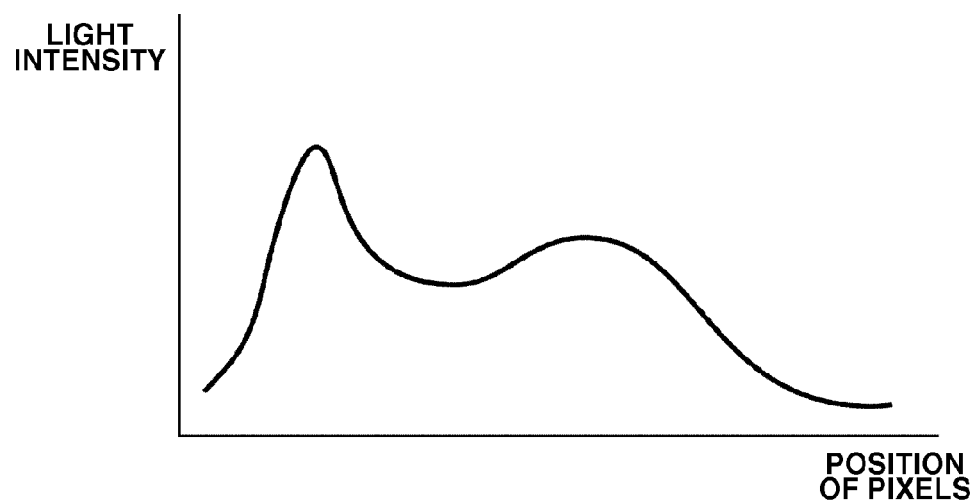
FIG. 4B illustrates frequency characteristics of a light source and an output signal of a sensor according to the first exemplary embodiment.

The interference light beams 114 are dispersed by the diffraction grating 107, but dispersion is performed under the same wavelength condition as a central wavelength and a band width of the light source. More specifically, a light with frequency characteristics as illustrated in FIG. 4A will be irradiated to the photoelectric conversion element arrays 109-1 to 109-3 (described below) of the line sensor 109 via the diffraction grating 107 and the lens 108. Then, as illustrated in FIG. 4B, the light wavelengths as a horizontal axis in FIG. 4A become 0 to 1023 pixel positions (the horizontal axis in FIG. 4B) of the photoelectric conversion element arrays 109-1 to 109-3 of the line sensor 109. A fiber end fixing portion 117 is used to fix positions at which three interference light beams 114 are incident on the diffraction grating 107.

Figure 1B:
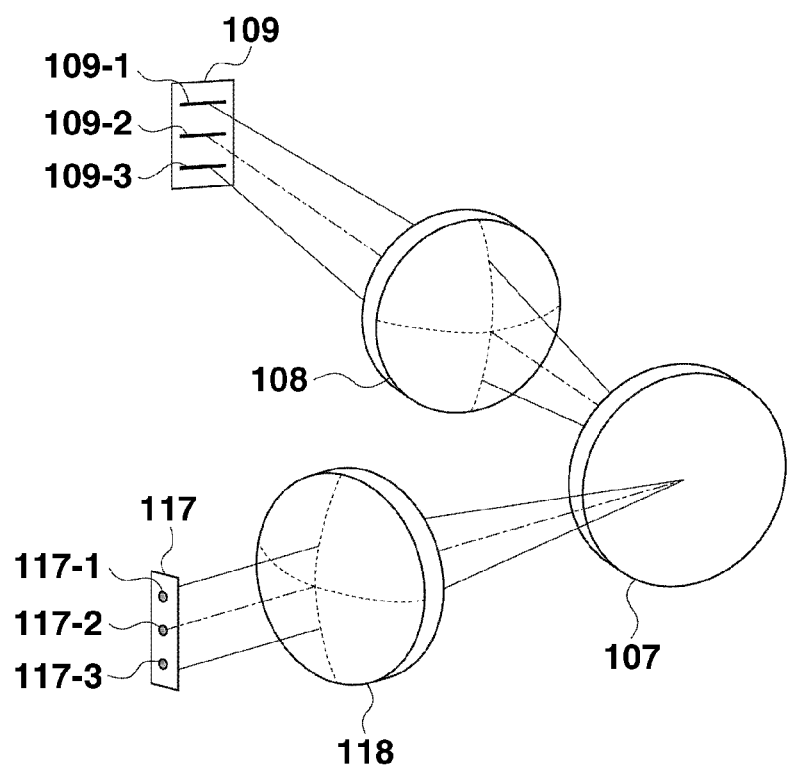
FIG. 1B illustrates an imaging apparatus according to the first exemplary embodiment.

FIG. 1B illustrates the three interference light beams 114 that form images on the line sensor 109. To the fiber end fixing portion 117, three optical fibers for transmitting each of the three interference lights 11 are fixed. The line sensor 109 includes three photoelectric conversion element arrays 109-1 to 190-3. The interference light beams 114 emitted from optical fibers 117-1 to 117-3 which are fixed to the fiber end fixing portion 117, respectively form images on the photoelectric conversion element arrays 109-1 to 109-3 via the lens 118, the diffraction grating 107, and the lens 108.

A line camera 119 includes a lens, a line sensor, an A/D conversion unit, and the like. Reflected lights from the retina irradiated with light beams emitted from an infrared light source (not illustrated), are reflected by a mirror 120 and guided to the line camera 119, and read out for each line. By causing the mirror 120 to rotate around a parallel axis relative to a line direction of the line camera 119, it becomes possible to read out two-dimensional images of the retina. In a controller (not illustrated), a piece of two-dimensional image is generated by connecting images together for each line. By repetitively operating the mirror 120 each time two-dimensional image is generated, it becomes possible to acquire continuous two-dimensional images of the retina.

Operations of the above-described units are controlled by the controller (not illustrated). The above-described controller is connected to a personal computer (PC), and a measurer operates the OCT apparatus using an input/output device such as a monitor, a mouse, and a keyboard connected to the PC.

Next, a selection method of imaging modes of the OCT apparatus according to the present exemplary embodiment will be described with reference to FIG. 2A. FIG. 2A is a selection screen of the imaging mode displayed on a monitor (sometimes referred to as display unit) attached to the OCT apparatus. A two-dimensional image 201 of the fundus is captured by the line camera 119. A macula 215 and an optic papilla 214 are illustrated in FIG. 2A.

B scan images 203 to 206 obtained by scanning the fundus with the respective beams are displayed at real time. The B scan image is obtained, before capturing tomographic images of the fundus, in order to perform a pint adjustment, and a position adjustment of the mirror 106, namely coherent gate adjustment, which reflects the reference light beam 112. Here, the images 203 to 206 are referred to as live B scan images. On the two-dimensional image 201 of the fundus, rectangles and lines are displayed for each of three laser beams (the details will be described below). The rectangles and lines indicate the scanning regions to be scanned with the respective three laser beams, and B scan lines scanned by the respective laser beams for obtaining the live B scan images.

Parameters of the imaging modes are set and displayed in a region 202. In this case, eight types of the imaging modes are displayed. The imaging modes to be displayed may be set by the measurer in advance, or may be displayed in descending order of imaging frequency from a past imaging history. Further, the parameters of the imaging modes can be selected on the monitor screen by the input unit such as the mouse, and changed at any time.

As the parameters of the imaging modes, the number of A scans, the number of B scans, an x range, a y range, the number of beams, and the number of times of imaging can be set. The x range represents an x direction of the fundus, i.e., an imaging region width in a horizontal direction relative to a head of a measured person. The y range represents a y direction of the fundus, i.e., an imaging region width in a vertical direction relative to the head of the measured person. The number of A scans represents resolution in the x direction of the fundus, and the number of B scans represents resolution in the y direction.

For example, if the x range=10 mm, the y range=5 mm, the number of A scans=500, the number of B scans=100 are set, 500 pieces of A scan data are combined at a pitch of 20 micrometer in the x direction to generate one piece of B scan image, and 100 pieces of the B scan images will be captured at a 50 micrometer pitch in the y direction.

The number of beams is the number of laser beams to be used for capturing an image of the fundus, and one beam and three beams can be selected in the apparatus according to the present exemplary embodiment. The number of times of imaging represents a repetitive number of scans of how many times the B scan line at the same position of the fundus will be captured. In SD-OCT apparatus, since tomographic images of the fundus will be created using fine image signals (interference signals), a method for reducing an effect of noises by performing processes for increasing the number of times of imaging and averaging the fine image signals is often employed. However, increase of the number of times of imaging may lengthen the imaging time period. In addition, a time period required to capture tomographic images of the fundus images according to the set parameters are displayed in the region 202.

Figure 5:
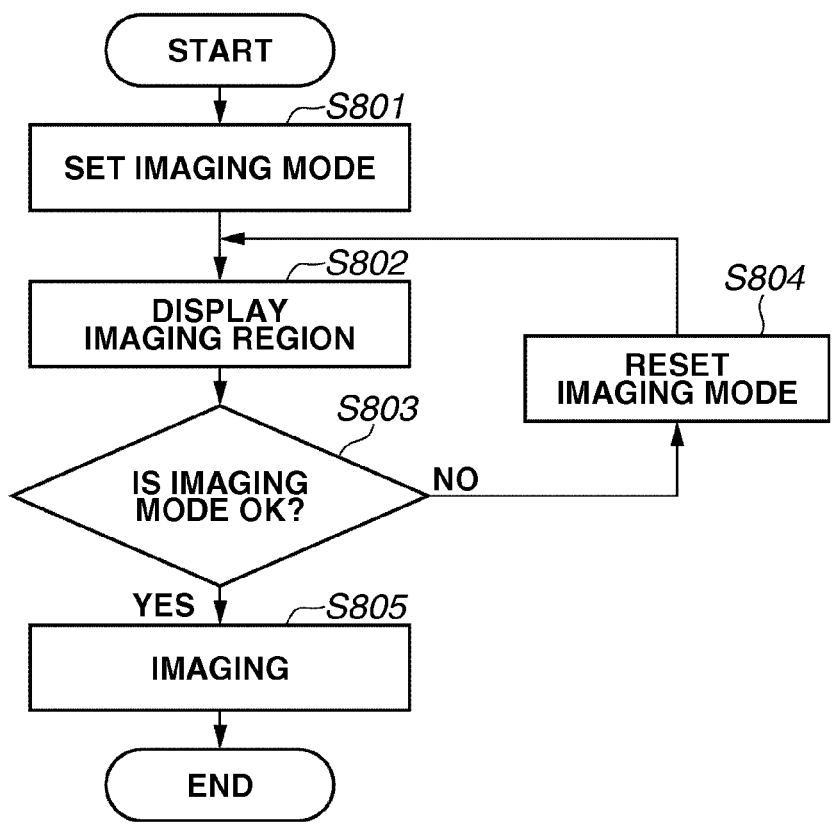
FIG. 5 is a flowchart illustrating an imaging method according to the first exemplary embodiment.

In the SD-OCT apparatus with the configuration described above, an operation according to the present exemplary embodiment will be described with reference to the flowchart in FIG. 5. In a state where a measured person is ready to be measured, first, in step S801, a measurer sets an imaging mode based on the measurer's operation. In the process, as an example, the measurer selects the imaging mode 2 including the number of A scans of 300, the number of B scans of 300, the x range of 10 mm, the y range of 10 mm, the number of laser beams of 3, and the number of times of imaging of 1. The imaging time period required for the imaging mode 2 is 0.75 seconds. Then, images as illustrated in FIG. 2A are displayed on an operation screen.

Figure 6A:
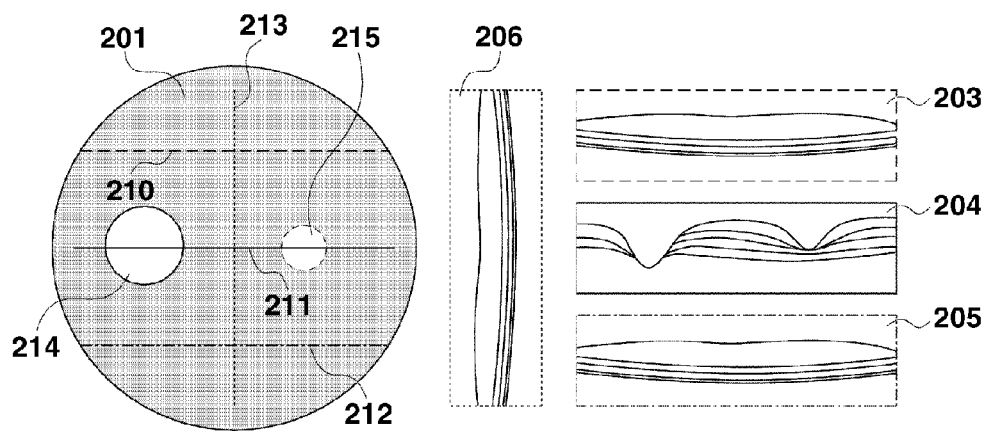
FIG. 6A illustrates a display of optical coherence tomographic images corresponding to the number of measurement light beams according to the first exemplary embodiment.

In the process, how three laser beams of the measurement light beams 111 each divide and scan the fundus is described with reference to FIG. 2B and FIG. 6A. In FIG. 2B and FIG. 6A, information unnecessary for the descriptions is deleted. As illustrated in FIG. 2B, the scanning regions of the three laser beams are respectively displayed in the order of scanning regions 207, 208, and 209 from the top. The scanning region 207, the scanning region 208, and the scanning region 209 are located on an upper part, a middle part, and a lower part of the fundus respectively. Further, the scanning region 207 and the scanning region 208, and also the scanning region 208 and the scanning region 208 are overlapped by 10% each in the y direction.

FIG. 6A illustrates a live B scan image in the mode selected in step S801. In FIG. 6A, a B scan line 210 indicates an imaging position of a live B scan image 203. Likewise, B scan lines 211, 212, and 213 indicate imaging positions of a live B scan image 204, a live B scan image 205, and a live B scan image 206, respectively.

As illustrated in FIG. 2B and FIG. 6A, a frame of the scanning region 207 in the upper part, a frame of the live B scan image 203 captured using a laser beam for scanning the scanning region 207 in the upper part, and the B scan line 210 thereof are indicated with the same dotted lines. Further, a frame of the scanning region 208 in the middle part, and a frame of the live B scan image 204 captured using a laser beam for scanning the scanning region 208 in the middle part, and the B scan line 211 thereof are indicated with solid lines.

Likewise, a frame of the scanning region 209 in the lower part, a frame of the live B scan image 205 captured using a laser beam for scanning the scanning region 209 in the lower part, and the B scan line 212 thereof are indicated with alternate long and short dash lines. Moreover, a frame of the live B scan image 206 in the y direction of the fundus, and the B scan line 213 thereof are indicated with thin dotted lines. According to the above described methods, it can be readily recognized that which laser beam has scanned which region, and which B scan line has been captured in the live B scan image currently displayed. In this example, solid lines or dotted lines are used to distinguish the regions or the like, but distinctions can be made by colors or the like for each laser beam such as red frames, or red lines.

Figure 7A:
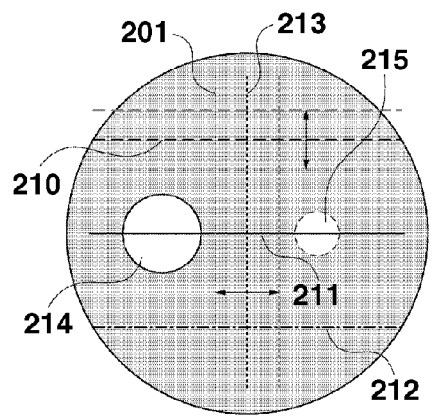
FIG. 7A illustrates a screen display according to the first and the second exemplary embodiments.

The live B scan images 203 to 206 to be first displayed after the selection of the imaging mode are the tomographic images at the middle part of the scanning region of each laser beam with respect to the x direction, and the tomographic image at the central part of the entire imaging region with respect to the y direction. As illustrated in FIG. 7A, when the B scan line 210 is clicked by a mouse (not illustrated), and moved up and down as indicated by an arrow in FIG. 7A, the live B scan image 203 corresponding to a position of the B scan line 210 after movement is displayed. Likewise, when the B scan line 213 is clicked and moved from side to side as indicated by the arrow in FIG. 7A, the live B scan image 206 corresponding to a position of the B scan line 213 after movement is displayed.

Then, in step S803, the measurer confirms the imaging regions on the fundus indicated in FIG. 2B, and determines whether the imaging mode currently selected is suitable for capturing tomographic images of the imaging regions of a patient i.e. the measured person.

For example, when the fundus images are captured with three laser beams, and three B scan images are combined, discontinuity will occur on the boundaries of the divided regions. Thus, if the boundary of the divided regions overlaps with a target region such as the periphery of a macula or an affected part, it is better to select the imaging mode using one laser beam.

Moreover, when the imaging region of the live B scan line is moved to the peripheral end, and it is confirmed that an image of the fundus end portion is not necessary to be captured, the imaging mode can be switched to the one in which only the periphery of the target region is captured with one laser beam. Here, a case will be described in which it is determined that the imaging of the fundus end portion of the patient is not necessary and the imaging mode 4 with small imaging region is selected in step S804.

Figure 3A:
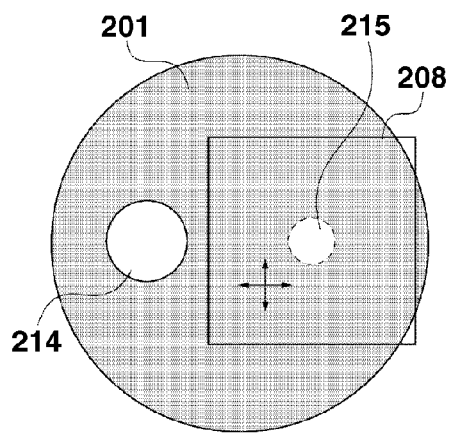
FIG. 3A illustrates an imaging mode according to the first and a second exemplary embodiment.

FIG. 3A illustrates the scanning region 208 at the time of setting the imaging mode 4, that is, the number of A scans of 300, the number of B scans of 300, the x range of 6 mm, the y range of 6 mm, the number of laser beams of 1, and the number of times of imaging of 1.

Figure 6B:
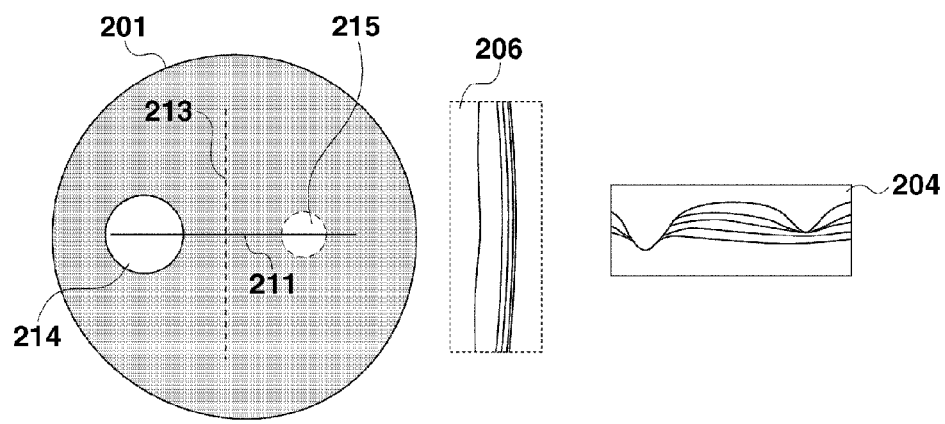
FIG. 6B illustrates a display of optical coherence tomographic images corresponding to the number of measurement light beams according to the first exemplary embodiment.

If the number of laser beams is set to 1 like the imaging mode 4, a second laser beam which scans the region 208 in the middle part is selected from among the three laser beams. This is because the second laser beam among the three laser beams which scan the region 208 in the middle part will pass through the central parts of the lenses 108 and 118, and thus is least affected by optical distortions at the lenses. FIG. 6B illustrates the live B scan image in the imaging mode 4 selected in step S804. In FIG. 6B, a B scan line 211 indicates an imaging position of the live B scan image 204.

When the scanning region 208 is clicked with the mouse (not illustrated), and moved up and down as indicated by an arrow in FIG. 3A, a position of the scanning region 208 can be moved on the fundus. As the actual movement, the scanning region is changed by adjusting under control of the controller a position of the optical system at the measured person side of the XY scanner 103. In this case, the position of the scanning region 208 is set so that a region centering on the macula 215 can be captured.

Figure 7B:
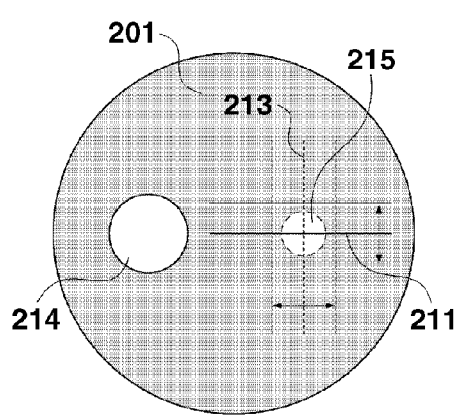
FIG. 7B illustrates a screen display according to the first and the second exemplary embodiments.

Moreover, the live B scan image 203 corresponding to the position of the B scan line 210 after movement is displayed. As illustrated in FIG. 7B, when the B scan line 211 is clicked with the mouse (not illustrated), and moved up and down as indicated by the arrow in FIG. 7B, the live B scan image 204 corresponding to the position of the B scan line 211 after movement is displayed. Likewise, when the B scan line 213 is clicked and moved from side to side as indicated with the arrow in FIG. 7B, the live B scan image 206 corresponding to the position of the B scan line 213 after movement is displayed.

As described above, the measurer selects the imaging mode, confirms the imaging regions and the live B scan image each time, and determines whether the selected imaging mode is suitable for symptoms of the patient i.e. the measured person or purpose of measurement. If it can be confirmed that the selected imaging mode is suitable for the purpose (YES in step S803), then in step S805, the measurer actually measures the tomographic images of the fundus as the measured object.

According to the present exemplary embodiment as described above, the imaging regions corresponding to the number of beams to be used for imaging can be displayed in a distinguishable manner on a two-dimensional image of the measured object. Accordingly, whether the selected imaging mode is suitable for the purpose of imaging can be readily confirmed. Further, the imaging mode suitable for the purpose of imaging can be readily changed.

When a fundus image of a measured person is captured, the scanning regions 207, 208, 209 of the laser beams on the operation screen as illustrated in FIG. 2B may be different from the scanning regions of the laser beams actually caused to be scanned on the fundus depending on individual differences such as an eye axis length and a refractive index of crystalline lens of the measured person, and a focal distance adjustment in the lens 104. In order to solve such variations, a step for calibrating the scanning regions of the laser beams may be included in the above-described exemplary embodiment.

More specifically, during operations of steps S801 and S802 in the above-described exemplary embodiment, the fundus may be scanned with the laser beams corresponding to the x range and the y range set in step S801, and scanning ranges of the laser beams used for scanning the fundus are measured in the line camera 119. If the actually measured scanning ranges of the laser beams are different from the scanning regions 207, 208, and 209 of the laser beams on the operation screen, it is only necessary to adjust the scanning regions of the laser beams to be displayed on the operation screen to the scanning regions of the measured laser beams. Conversely, an amount of rotation of the XY mirror 103 may be controlled so that the scanning regions 207, 208, and 209 of the laser beams displayed on the operation screen coincide with the scanning ranges of the laser beams actually used for scanning the fundus.

Figure 7C:
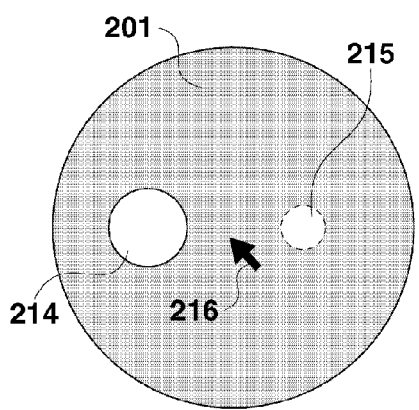
FIG. 7C illustrates a screen display according to the first and the second exemplary embodiments.
Figure 8:
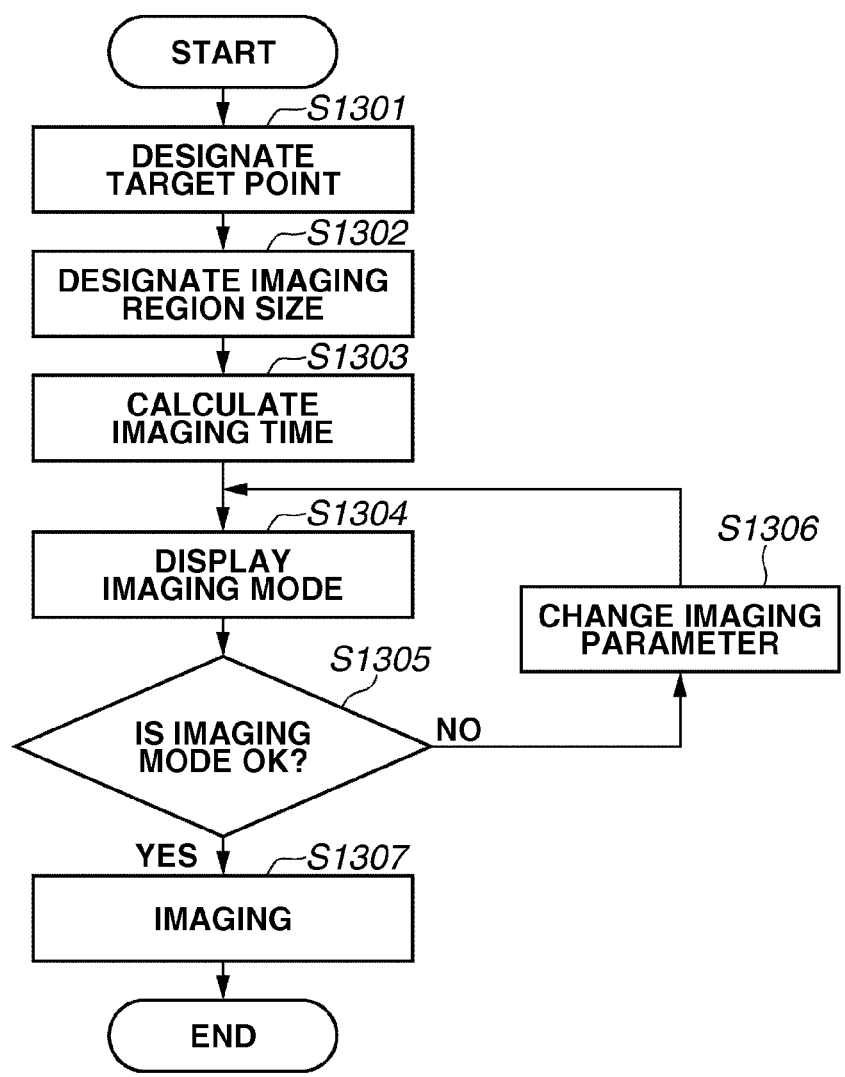
FIG. 8 is a flowchart illustrating an imaging method according to the second exemplary embodiment.

Next, a method for automatically selecting the imaging modes will be described as a second exemplary embodiment with reference to the flowchart in FIG. 8. First, in step S1301, the measurer designates a target point on a two-dimensional image 201 of the fundus with a mouse cursor 216 as illustrated in FIG. 7C. Next, in step S1302, the measurer sets parameters of the imaging mode by designating an imaging region size in a setting/display unit.

At this time, if the x range and the y range both are set to 100 per 1 mm in advance, i.e., the resolution in the x direction and the y direction are set to 100(1/mm), then the number of A scans and the number of B scans will be set in conjunction with the designation of the x range and the y range. Although a case where the resolution is set to 100 for both the x direction and the y direction will be described, this value may be arbitrarily set. Moreover, although the number of times of imaging is set to one, this value can also be arbitrarily changed.

Next, in step S1303, the imaging time period in the case that the number of the laser beams is one and the case that the number of the laser beams is three are calculated from the set parameters in the PC. It is difficult to cause a patient as the measured person to stay his/her eye still at one location. Therefore, in this case, a limitation not to allow selecting the imaging mode in which the imaging time period exceeds three seconds is set.

When the number of the laser beams is plural, a discontinuity of the boundaries between the divided imaging regions may occur. Therefore, an optimal imaging mode can be selected, depending on whether priority is given to capturing images in a short time or capturing images without discontinuity. In the present exemplary embodiment, if priority is given to the capturing of images without discontinuity and an imaging time period with one laser beam is within three seconds as the limit time, the imaging mode using one laser beam is supposed to be selected.

Figure 3B:
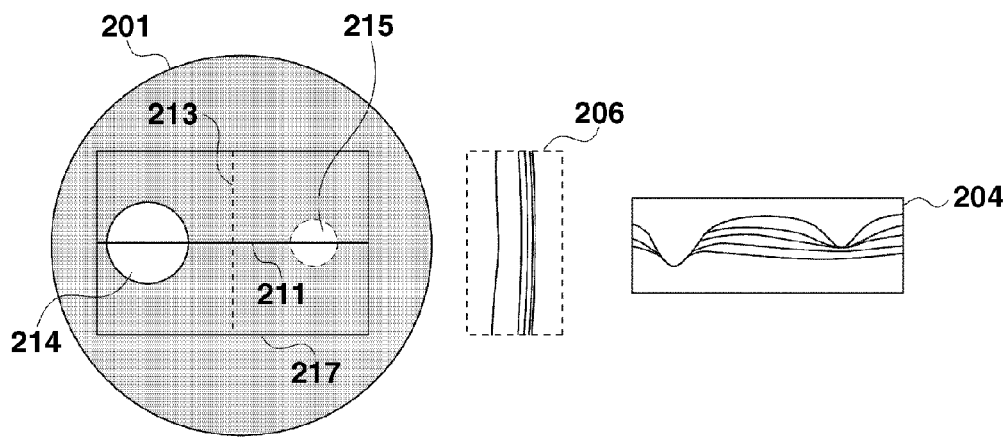
FIG. 3B illustrates an imaging mode according to the first and the second exemplary embodiments.

Next, in step S1304, the monitor indicates the conditions set to the imaging mode 1, and displays imaging regions and the live B scan images, as illustrated in FIG. 3B. In this case, since the imaging mode using one laser beam is selected from the set conditions, the imaging region 208 scanned with the second laser beam among the three laser beams for scanning the region in the center part, the live B scan image 204 acquired by the second laser beam among the three laser beams for scanning the region in the center part, and the live B scan image 206 in the y direction are displayed.

Next, in step S1305, the measurer determines whether imaging in the imaging mode displayed in step S1304 meets the purpose by moving the live B scan lines 211 and 213. If the selected imaging mode does not meet the purpose (NO in step S1305), then in step S1306, similarly to the first exemplary embodiment, the controller resets the imaging mode. Then, the processing in steps S1304 to S1306 is repeated until an imaging mode which meets the purpose of imaging is found. Finally, in step S1307, if the imaging mode which meets the purpose of imaging can be set, the OCT apparatus captures tomographic images of the fundus.

Figure 7D:
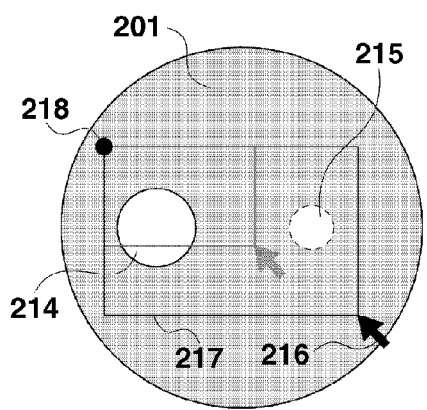
FIG. 7D illustrates a screen display according to the first and the second exemplary embodiments.

In the present exemplary embodiment, a method for setting the imaging region by designating a center point of a desired imaging region with the mouse cursor and setting the x range and the y range with numerical values is described. However, a method for designating an imaging region 217 by moving the mouse cursor from a starting point 218 to an oblique direction while clicking as illustrated in FIG. 7D, may be used.

According to the present exemplary embodiment as described above, since the imaging mode can be also selected by setting a region, if an operator does not understand various imaging modes, the operator can select an appropriate imaging mode and operate the apparatus easily.

In the second exemplary embodiment, priority for selecting the imaging mode is given to the conditions of the imaging region, the imaging time period, and the number of beams, in this order. In a third exemplary embodiment, the measurer can arbitrarily determine the priority of all parameters for determining an imaging mode, such as imaging region, an imaging time period, the number of beams, the number of times of imaging, and resolution.

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2010-082804 filed Mar. 31, 2010, which is hereby incorporated by reference herein in its entirety.

The invention claimed is:

1. An imaging apparatus for acquiring a plurality of optical coherence tomographic images of an inspection object based on a plurality of combined light beams obtained by combining a plurality of return light beams from the inspection object irradiated with a plurality of measurement light beams and a plurality of reference light beams corresponding to the plurality of measurement light beams, the imaging apparatus comprising:
  an intersection image acquisition unit configured to acquire an intersection image of the inspection object in a direction intersecting a direction in which the inspection object is irradiated with the plurality of measurement light beams;
  an intersection image display control unit configured to cause a display unit to display the intersection image;
  a scanning range display control unit configured to cause the display unit to display scanning ranges of each of the plurality of measurement light beams on the intersection image,
  a position display control unit configured to cause the display unit to display acquired positions of the plurality of optical coherence tomographic images on the intersection image;
  a tomographic image display control unit configured to cause the display unit to display the plurality of optical coherence tomographic images in real time;
  a plurality of mirrors separately disposed in optical paths of the plurality of reference light beams; and
  an adjustment unit configured to adjust positions of the plurality of minors in directions of optical axes of the optical paths of the plurality of reference light beams when the plurality of the optical coherence tomographic images is displayed on the display unit in real time.

2. The imaging apparatus according to claim 1, wherein the scanning range display control unit causes the display unit to display the scanning ranges with different colors or shapes.

3. The imaging apparatus according to claim 1, wherein the inspection object is a fundus of an eye to be examined, and
  the intersection image is any one of a two-dimensional image of a surface of the fundus, an integrated image obtained by integrating at least a portion of the optical coherence tomographic images in a depth direction of the fundus, and the optical coherence tomographic images in a substantially vertical direction to the depth direction of the fundus.

4. The imaging apparatus according to claim 1, further comprising:
  a selection unit configured to select at least one of a plurality of imaging modes with different imaging conditions; and
  an acquisition unit configured to acquire the optical coherence tomographic images according to the imaging mode selected by the selection unit.

5. The imaging apparatus according to claim 4, further comprising an imaging condition display control unit configured to cause the display unit to display a list of the plurality of imaging modes and an image including a function of the selection unit.

6. The imaging apparatus according to claim 4, wherein at least one imaging mode among the plurality of imaging modes is set so that the number of measurement light beams irradiated to the inspection object is different from that of the other imaging modes.

7. The imaging apparatus according to claim 4, wherein at least one imaging mode among the plurality of imaging modes is set so that at least one value among a size of the scanning range, the number of times of imaging, and an imaging time period is different from those in the other imaging modes.

8. A method for capturing optical coherence tomographic images of an inspection object using an imaging apparatus according to claim 1, the method comprising:
  inputting a signal to be displayed on the display unit; and
  displaying information based on the input signal on the display unit.

9. The imaging apparatus according to claim 1, further comprising an irradiation unit configured to simultaneously irradiate the inspection object with the plurality of measurement light beams.

10. The imaging apparatus according to claim 1, further comprising a single scanning unit configured to simultaneously scan the inspection object with the plurality of measurement light beams.

11. The imaging apparatus according to claim 1, wherein the acquired positions are movable separately from each other.

12. An imaging method for acquiring a plurality of optical coherence tomographic images of an inspection object based on a plurality of combined light beams obtained by combining a plurality of return light beams from the inspection object irradiated with a plurality of measurement light beams and a plurality of reference light beams corresponding to the plurality of measurement light beams, the method comprising:
  displaying an intersection image of the inspection object in a direction intersecting a direction in which the inspection object is irradiated with the plurality of measurement light beams;
  displaying scanning ranges of each of the plurality of measurement light beams on the display unit on the intersection image,
  displaying, on the display unit, acquired positions of the plurality of optical coherence tomographic images on the intersection image;
  controlling a tomographic image display configured to cause the display unit to display the plurality of optical coherence tomographic images in real time; and
  adjusting positions of a plurality of mirrors in directions of optical axes of the optical paths of the plurality of reference light beams when the plurality of the optical coherence tomographic images is displayed on the display unit in real time, the plurality of mirrors disposed separately in the optical paths of the plurality of reference light beams.

13. A computer-readable medium storing a program for causing a computer to execute the method according to claim 12.

14. The imaging method according to claim 12, wherein the acquired positions are movable separately from each other.

15. An imaging method for acquiring a plurality of optical coherence tomographic images of an inspection object based on a combined light beam obtained by combining a return light beams from the inspection object irradiated with a measurement light beam and a reference light beam corresponding to the measurement light beams, the method comprising:
  determining a size of a region for acquiring the plurality of optical coherence tomographic images;
  calculating a time to acquire the plurality of optical coherence tomographic images in a region of the determined size;
  selecting any one of a plurality of imaging modes including at least a mode for acquiring the plurality of optical coherence tomographic images using a plurality of measurement light beams and a mode for acquiring the plurality of optical coherence tomographic images using one of the plurality of measurement light beams;
  restricting selection so as not to select an imaging mode in which the calculated time exceeds a threshold value; and
  acquiring the optical coherence tomographic images according to an imaging mode selected from the plurality of imaging modes except for the restricted imaging mode.

16. A computer-readable medium storing a program for causing a computer to execute the method according to claim 15.

17. An imaging apparatus for acquiring a plurality of optical coherence tomographic images of an inspection object based on a combined light beam obtained by combining a return light beams from the inspection object irradiated with a measurement light beams and a reference light beam corresponding to the measurement light beam, the imaging apparatus comprising:
  determination unit configured to determine a size of a region for acquiring the plurality of optical coherence tomographic images;
  calculation unit configured to calculate a time to acquire the plurality of optical coherence tomographic images in a region of the determined size;
  a selection unit configured to select any one of a plurality of imaging modes including at least a mode for acquiring the plurality of optical coherence tomographic images using a plurality of measurement light beams and a mode for acquiring the plurality of optical coherence tomographic images using one of the plurality of measurement light beams;
  restriction unit configured to restrict selection so as not to select an imaging mode in which the calculated time exceeds a threshold value; and
  an acquisition unit configured to acquire the optical coherence tomographic images according to an imaging mode selected from the plurality of imaging modes except for the restricted imaging mode.

18. The imaging apparatus according to claim 17, further comprising an imaging condition display control unit configured to cause a display unit to display a list of the plurality of imaging modes and an image including a function of the selection unit.

19. The imaging apparatus according to claim 17, wherein at least one imaging mode among the plurality of imaging modes is set so that the number of measurement light beams irradiated to the inspection object is different from that of the other imaging modes.

20. An imaging apparatus for acquiring a plurality of optical coherence tomographic images of an object based on combined lights obtained by combining return lights from the object irradiated with measurement lights and reference lights corresponding to the measurement lights, the imaging apparatus comprising:
  a display control unit configured to cause a display unit to display the plurality of optical coherence tomographic images in real time;
  a plurality of mirrors separately disposed in optical paths of the reference lights; and
  an adjustment unit configured to adjust positions of the plurality of mirrors in directions of optical axes of the optical paths when the plurality of the optical coherence tomographic images is displayed on the display unit in real time.

21. The imaging apparatus according to claim 20, wherein the display control unit causes the display unit to display the plurality of optical coherence tomographic images corresponding to the adjusted positions in real time.

22. The imaging apparatus according to claim 20, further comprising an irradiation unit configured to simultaneously irradiate the object with the measurement lights.

23. The imaging apparatus according to claim 20, further comprising a single scanning unit configured to simultaneously scan the object with the measurement lights.

24. The imaging apparatus according to claim 20, further comprising an intersection image acquisition unit configured to acquire an intersection image of the object in a direction intersecting a direction in which the object is irradiated with the measurement lights,
  wherein the display control unit is configured to cause a display unit to display the intersection image and display, on the intersection image, acquired positions of the plurality of optical coherence tomographic images in real time.

25. The imaging apparatus according to claim 24, wherein the display control unit causes the display unit to display the acquired positions with at least one of different colors and different shapes.

26. The imaging apparatus according to claim 24, wherein the acquired positions are movable separately from each other.

27. The imaging apparatus according to claim 24,
wherein the object is a fundus of an eye to be examined, and
wherein the intersection image is any one of a two-dimensional image of a surface of the fundus, an integrated image obtained by integrating at least a portion of the optical coherence tomographic images in a depth direction of the fundus, and the optical coherence tomographic images in a substantially vertical direction to the depth direction of the fundus.

28. An imaging method for acquiring a plurality of optical coherence tomographic images of an object based on combined lights obtained by combining return lights from the object irradiated with measurement lights and reference lights corresponding to the measurement lights, the method comprising:

displaying, on a display unit, the plurality of optical coherence tomographic images in real time; and adjusting positions of a plurality of mirrors in directions of optical axes of optical paths of the reference lights when the plurality of the optical coherence tomographic images is displayed on the display unit in real time, the plurality of mirrors disposed separately in the optical paths of the reference lights.

29. A computer-readable medium storing a program for causing a computer to execute the method according to claim 28.

* * * * *